US00PP08065P

United States Patent [19]

Kriloff

[11] Patent Number: Plant 8,065

[45] Date of Patent: Dec. 22, 1992

[54] ROSE PLANT — KRIBOROU VARIETY

[75] Inventor: Michel Kriloff, Antibes, France

[73] Assignee: Georges Delbard Société Civile Agricole, Malicorne, France

[21] Appl. No.: 628,351

[22] Filed: Dec. 17, 1990

[30] Foreign Application Priority Data

Dec. 18, 1989 [FR] France ..... 9084

[51] Int. Cl.[5] ..... A01H 5/00

[52] U.S. Cl. ..... Plt./20

[58] Field of Search ..... Plt./20, 21, 28, 29

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly forms attractive double flowers which are medium red in coloration. Such flowers are long lasting and comprise petals which detach cleanly. The plant exhibits an upright growth habit, forms semi-vigorous to vigorous vegetation, forms many thorns which are of varied lengths, and is well suited for greenhouse forcing for cut flower production. Additionally, the plant is very resistant to diseases.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety resulted from the crossing of the SONIA variety (U.S. Plant Pat. No. 3,095) with the Chamade-Kripordi variety (non-patented in the United States). The SONIA variety sometimes is known as the Sweet Promise variety. The male parent (i.e., the pollen parent) was the Royal Red variety (non-patented in the United States). The parentage of the new variety can be summarized as follows:

(Sonia × Chamade-Kripordi) × Royal Red.

The seeds resulting from the above pollination were sown and 257 small plantlets were obtained which were physically and biologically different from each other. Selective study resulted in the identification of a single plant of the new variety.

It was found through careful study that the new variety of the present invention can be characterized by the following combination of characteristics:

(a) from a physical point of view it forms bronze green mature wood, assumes an upright growth habit, forms many thorns of varied lengths, and forms attractive double flowers with consistent petals which are medium red in coloration, and (b) from the biological point of view it forms semi-vigorous to vigorous vegetation, produces flowers in abundance, exhibits the ability readily to be forced, is very resistant to diseases, and forms long lasting flowers comprising petals which detach cleanly.

The new variety can be readily distinguished from the varieties utilized during its creation as confirmed during observations made at Hyéres, France when grown under standard greenhouse conditions. Representative observations are summarized below where reference is made to The R.H.S. Colour Chart.

| | New Variety of Present Invention | SONIA Variety | CHAMADE-KRIPORDI Variety | ROYAL RED Variety |
|---|---|---|---|---|
| Petal Color-Inside Surface | Red Group 43A to 44B | Red Group 38A | Red Group 43B | Red Group 46A |
| Petal Color-Outside Surface | Red Group 45C to 46B | Red Group 38C | Red Group 52A to 52B | Red Group 46B |
| Typical Length of Stems | 70 to 90 cm. | 40 to 60 cm. | 70 to 80 cm. | 40 to 60 cm. |
| Average Vase Life | 10 days | 7 days | 5 days | 7 days |
| Thorns | very strong and numerous | medium | strong | medium |

When grown under greenhouse conditions the new variety has exhibited no susceptibility to powdery mildew and downy mildew.

The new variety well meets the needs of the horticultural industry and is particularly well suited for the production of long-lasting cut flowers.

The new variety has been found to undergo asexual propagation and can be readily reproduced by the grafting of an eye, the rooting of cuttings, and by in vitro cultivation. Such asexual propagation has been carried out at Antibes, Hyéres, and Commentry, France. The characteristics of the new variety have been found to be strictly transmissible by such asexual propagation from one generation to another.

The new variety has been named the Kriborou variety.

BRIEF DESCRIPTION OF THE PHOTOGRAPH

The accompanying photograph shows as nearly true as it is reasonably possible to make the same in a color illustration of this character typical specimens of the plant parts of the new variety. The rose plants of the new variety were grown under glass at Antibes France.

DETAILED DESCRIPTION

Figures 1, 2, 3, 4, 5, 6, 7, 8, 9, 10, 11, 12, 13, 14, 15, 16:
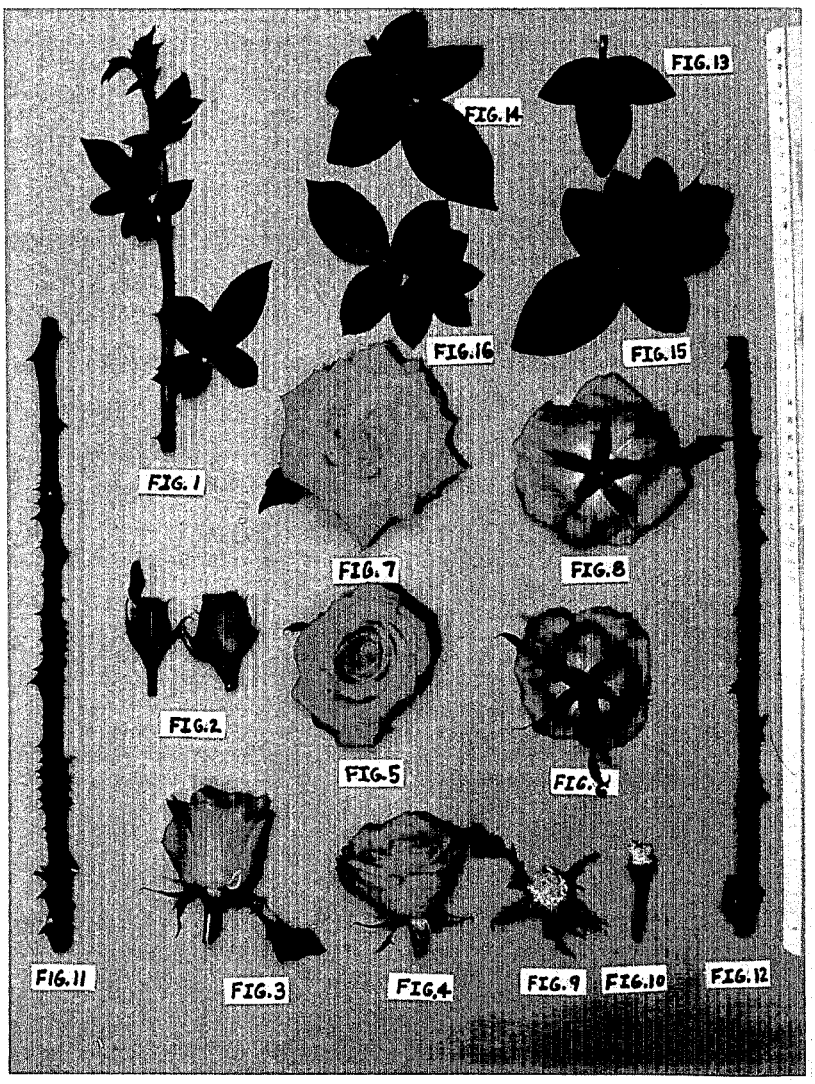
FIG. 1 illustrates a specimen of a young shoot.
FIG. 2 illustrates specimens of two floral buds at the opening of the sepals.
FIG. 3 illustrates a specimen of a floral bud at the opening of the petals.
FIG. 4 illustrates a specimen of a flower in the course of opening.
FIG. 5 illustrates a specimen of an open flower — plan view — obverse.
FIG. 6 illustrates a specimen of an open flower — plan view — reverse.
FIG. 7 illustrates a specimen of a fully open flower — plan view — obverse.
FIG. 8 illustrates a specimen of a fully open flower — plan view — reverse.
FIG. 9 illustrates a specimen of a floral receptacle showing the arrangement of the stamens and pistils.
FIG. 10 illustrates a specimen of a floral receptacle showing the arrangement of the pistils (sepals and stamens removed)
FIG. 11 illustrates a specimen of a flowering stem.
FIG. 12 illustrates a specimen of a main branch.
FIG. 13 illustrates a specimen of a leaf with three leaflets — plan view — upper surface.
FIG. 14 illustrates a specimen of a leaf with five leaflets — plan view — upper surface.
FIG. 15 illustrates a specimen of a leaf with seven leaflets — plan view — upper surface.
FIG. 16 illustrates a specimen of a leaf with seven leaflets — plan view — under surface.

The chart used in the identification of the colors is that of The Royal Horticultural Society (R.H.S. Colour Chart). The description is based on the observation of plants grown under glass at Antibes France. The coloration in common terms sometimes also is provided.

Class: Hybrid Tea.

Plant:

*Height.*—Approximately 160 cm. When pruned to a height of 85 cm. under greenhouse conditions, floral stems are formed having a length of approximately 50 to 100 cm., and most typically having a length of 70 to 90 cm., and a mean length of approximately 80 cm.

*Habit.*—Upright.

Branches:

*Color.*—Young shoots: when approximately 20 cm. long are Greyed-Purple Group 183B with under coloration of Yellow-Green Group 152A. Floral stems: Yellow-Green Group 146B and shaded with reddish-brown coloration. Mature wood: Yellow-Green Group 146A.

*Thorns.*—Configuration: convex upper edge and deep concave lower edge. Quantity: Very numerous, generally range in length from 1 to 12 mm., and generally can be divided into two groups, with one group commonly ranging in length from 1 to 3 mm., and one group commonly ranging in length from 8 to 12 cm. Color on young shoot: Greyed-Purple Group 187A and 187B. Color on floral stems: Greyed-Purple Group 187B. Color on mature wood: Greyed-Orange Group 165B.

*Leaflets.*—Number: 3, 5 and 7. Size: Medium to large. Shape: convex in cross section with very weak margin undulation. Serration: strong, singular and regular. Texture: consistent. Color on young shoots: when approximately 20 cm. long, Greyed-Purple Group 187A with reddish under color on upper surface and Greyed-Purple Group 187B on under surface. Color on floral stems: Yellow-Green Group 147A on upper surface and Yellow-Green Group 147B on under surface. Color on mature wood: Yellow-Green Group 147A on upper surface and Yellow-Green Group 147B on under surface. General appearance: a medium glossiness commonly is present on the upper surface of the leaflets. Terminal leaflets: medium to long in length (e.g., approximately 7 cm.) and medium in width (e.g., approximately 3.5 to 4.5 cm.), have an obtuse to rounded base, and are borne on petioles of medium length (e.g., approximately 2 cm.).

Inflorescence:

*Flowering habit.*—Abundant and almost continuous. When grown under greenhouse conditions, the new variety forms one blossom per stem on approximately 80 percent of the stems, forms two blossoms per stem on approximately 20 percent of the stems, and very rarely forms three blossoms per stem. When grown under field cultivation, the new variety commonly forms one blossom per stem on approximately 20 percent of the stems, two blossoms per stem on approximately 20 percent of the stems, three blossoms per stem on approximately 20 percent of the stems, four blossoms per stem of approximately 20 percent of the stems, and five blossoms per stem on approximately 20 percent of the stems.

*Peduncle.*—Average to many hairs or prickles are present.

*Sepals.*—Sepal extensions are highly variable in occurrence and length. On a given flower commonly one or two sepals have no extensions or only weak extensions, one or two sepals have medium-length extensions, and one sepal has a long or very long extension (as illustrated). Color: commonly Yellow-Green Group 144D on the upper surface and 144B on the under surface.

*Flower.*—Time: flowering begins medium to late. Under greenhouse conditions when pruned in January, the first flowers can be cut approximately 75 days later. This can be compared to the quickly reflowering SONIA variety which commonly produces flowers suitable for cutting after approximately 60 days. Shape: double, the upper and lower parts of the fully opened flower are of flattened convex configurations, when viewed from the side and when viewed from above the flower is round to irregularly rounded. Diameter: very large approximately 10 to 14 cm. in diameter with a mean diameter of 12 cm. and a standard deviation of 2 cm. Petal size: relatively large (e.g., approximately 5.5 cm.). Petal shape: the first 2 to 3 well-developed outermost petals tend to be of a very broad obovate configuration and may be removed and discarded, the margins possess medium to strong reflexing, and the margin undulation is weak to medium. Petal color: the marginal zone of the inner side is Red Group 44B to Red Group 45B, the middle zone of the inner side is Red Group 43A to Red Group 44B, the marginal zone of the outer side is Red Group 45C to Red Group 46B, the middle zone of the outer side is Red Group 45C to Red Group 46C, a spot at the base of the inner and outer sides is very small to small in size and is Yellow Group 6C to Yellow-Green Group 150D on the inner side and Yellow Group 3D to Yellow-Green Group 150D on the outer side. Fragrance: none. Lasting quality: long and commonly last 7 to 15 days (average 10 days) in quality form when either on the plant or when cut and placed in a vase. Petal number: approximately 30 to 40 on average. Petal drop: good. Filaments: the predominant coloration is Yellow Group 6D near the base and Red Group 53D close to the anthers. Anthers: Orange Group 24C. Pollen: Normal quantity, and the coloration is light yellow and varies in shade with the stage of maturation. Stigmas: generally of a slightly greater height than the anthers and Yellow-Orange Group 14C. Styles: medium to long in length, hairiness at the upper half is weak to medium, predominately Yellow-Green Group 154D near the base and Orange-Red Group 31B at the top. Receptacle: medium in size, and in longitudinal section, it is in the shape of a funnel. Hips: are rarely formed, and when present are pitcher-shaped and commonly have a diameter of approximately 25 mm.

Development:

*Vegetation.*—Semi-vigorous to vigorous.
*Blooming.*—Abundant and almost continuous.
*Resistance to diseases.*—Very good.
*Aptitude to forcing.*—Very good.

It should be emphasized that the plants of the variety described herein were grown under glass for cut flower production, and that when the new variety is grown out-of-doors it commonly exhibits typical Hybrid Tea characteristics coupled with the formation of some multiple buds per stem.

I claim:

1. A new and distinct variety of Hybrid Tea rose plant characterized by the following combination of characteristics:

(a) from a physical point of view forms bronze green mature wood, assumes an upright growth habit, forms many thorns of varied lengths, and forms attractive semi-double flowers with consistent petals which are medium red in coloration, and
(b) from the biological point of view forms semi-vigorous to vigorous vegetation, produces flowers in abundance, exhibits the ability readily to be forced, is very resistant to diseases, and forms long lasting flowers comprising petals which detach cleanly;

substantially as herein shown and described.

* * * * *